United States Patent [19]

Del Vecchio et al.

[11] Patent Number: 5,728,522
[45] Date of Patent: Mar. 17, 1998

[54] OLIGONUCLEOTIDES AND NUCLEIC ACIDS FOR DETECTION OF UREAPLASMA UREALYTICUM

[75] Inventors: Vito G. Del Vecchio, Scranton, Pa.; Louis E. Blouse, Jr.; Ferne K. McCleskey, both of San Antonio, Tex.

[73] Assignee: Research Corporation Technologies, Inc., Tucson, Ariz.

[21] Appl. No.: 228,913

[22] Filed: Apr. 18, 1994

Related U.S. Application Data

[63] Continuation of Ser. No. 874,842, Apr. 27, 1992.
[51] Int. Cl.$^6$ .............................. C12Q 1/68; C12P 19/34
[52] U.S. Cl. .............................. 435/6; 435/91.2; 935/77; 935/78
[58] Field of Search ................... 435/6, 91.2; 935/77, 935/78; 536/24.32

[56] References Cited

U.S. PATENT DOCUMENTS 4,683,195  7/1987  Mullis et al. ........................... 435/6

FOREIGN PATENT DOCUMENTS 8803957  6/1988  WIPO ................................... 435/6

OTHER PUBLICATIONS

Roberts et al., Lsr. J. Med. Sci. 23(6):618–620 (Jun. 1987).
Rogers et al., PNAS USA 82:1160–1164 (Feb. 1985).
Weisburg et al., J. Bact. 171(12):6455–6467 (Dec. 1989).
Richards et al. (1991) Gene Probes, *Current Opinion in Biotechnology* 2: 76–85.
Brogan et al. (1992) Development of a DNA Probe for *Ureaplasma urealyticum*, *Molecular and Cellular Probes* 6:411–416.
Blanchard, A. (1990) *Ureaplasma urealyticum*Urease Genes; Use of a UGA Tryptophan Codon, *Molecular Microbiology* 4(4):669–676.
Roberts et al. (1987) DNA Probes for the Detection of Mycoplasmas in Genital Specimens, *Israel Journal of Medical Sciences* 23:618—620.
Gonzales et al. (1991) A Non–isotopic DNA Probe for the Specific Detection of Ureaplasma, *Abstr. Gen. Meet. Am. Soc. Microbiol.*, vol. 91, p.81.
Hammond et al. (1991) Biotype Specific Probes for *Ureaplasma urealyticum*, *Abstr. Gen. Meet.Am. Soc. Microbiol.*, vol. 91, p. 81.
Wright et al. (1990) The Polymerase Chain Reaction: Miracle or Mirage? A Critical Review of its Uses and Limitations in Diagnosis and Research, *Journal of Pathology* 162:99–117.

*Primary Examiner*—Stephanie W. Zitomer
*Attorney, Agent, or Firm*—Scully, Scott, Murphy & Presser

[57] ABSTRACT

The present invention is directed to a rapid and sensitive method for detecting *Ureaplasma urealyticum* using *U. urealyticum*-specific probes and oligonucleotides. In particular a target sequence can be amplified by in vitro nucleic acid amplification techniques or directly detected by nucleic acid hybridization using the subject probes and oligonucleotides. *U. urealyticum*-specific nucleic acids which do not recognize or hybridize to genomic nucleic acid of Mycoplasma species are also provided.

12 Claims, 4 Drawing Sheets

SEQ ID NO:1

5'ATCTGATGAAACTAAATTTATTGTTGTTAAAGTTTTAGATATTGGTGATGAAAAACAACA

AATGGTTGTTTATGATGAATTACGAATTTCAAATTTAATTAAGAATTCAAACTCTGATAAAA

GAAGTTATATCATGGAATATTATGAATATTTCGAAAGTGGTTCATTAGAAACTGATGATAAA

CGAATTTACATTGTTTTTGAATATATTGATGGTTTAACATTGCGTGAATATCTTGATGAATT

TAAAACAGTTACTTATGTTAAAGCTGTGAATATCGTCAGGTGCT3'.

SEQ ID NO:2: 5'-ACTAAATTTATTGTTGTTAA-3';

SEQ ID NO:3: 5'-CAATGTAAATTCGTTTATCA-3';

FIG. 1a

SEQ ID NO:4: 5'-TCGAACGAAGCCTTTTAGGC-3';

SEQ ID NO:5: 5'-CCAAAAGCGTCGCAAACGCG-3';

SEQ ID NO:6: 5'-TACAGTTTTTGATACAGCTA-3';

SEQ ID NO:7: 5'-CAGTGATAGTCCAAGTTGGC-3';

SEQ ID NO:8: 5'-TGTAGTGATCATATCAGAGTG-3'; and

SEQ ID NO:9: 5'-GACCTATTTTACTTGCGCTAT-3'.

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 290 base pairs
( B ) TYPE: nucleic acid
( C ) STRANDEDNESS: both
( D ) TOPOLOGY: linear ( i i ) MOLECULE TYPE: DNA (genomic)

( x i ) SEQUENCE DESCRIPTION: SEQ ID NO:1:

```
ATCTGATGAA  ACTAAATTTA  TTGTTGTTAA  AGTTTTAGAT  ATTGGTGATG  AAAAACAACA      60

AATGGTTGTT  TATGATGAAT  TACGAATTTC  AAATTTAATT  AAGAATTCAA  ACTCTGATAA     120

AAGAAGTTAT  ATCATGGAAT  ATTATGAATA  TTTCGAAAGT  GGTTCATTAG  AAACTGATGA     180

TAAACGAATT  TACATTGTTT  TTGAATATAT  TGATGGTTTA  ACATTGCGTG  AATATCTTGA     240

TGAATTTAAA  ACAGTTACTT  ATGTTAAAGC  TGTGAATATC  GTCAGGTGCT                 290
```

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

```
ACTAAATTTA  TTGTTGTTAA                                                      20
```

( 2 ) INFORMATION FOR SEQ ID NO:3:

( i ) SEQUENCE CHARACTERISTICS:
( A ) LENGTH: 20 base pairs
( B ) TYPE: nucleic acid
( C ) STRANDEDNESS: single ( D ) TOPOLOGY: linear ( i i ) MOLECULE TYPE: DNA (genomic)

( x i ) SEQUENCE DESCRIPTION: SEQ ID NO:3:

CAATGTAAAT TCGTTTATCA                    20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:4:

TCGAACGAAG CCTTTTAGGC                    20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:5:

CCAAAAGCGT CGCAAACGCG                    20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:6:

TACAGTTTTT GATACAGCTA                    20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:7:

CAGTGATAGT CCAAGTTGGC                    20

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:8:

TGTAGTGATC ATATCAGAGT G                                                       21

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:9:

GACCTATTTT ACTTGCGCTA T                                                       21

OLIGONUCLEOTIDES AND NUCLEIC ACIDS FOR DETECTION OF UREAPLASMA UREALYTICUM

This is a continuation of copending application(s) Ser. No. 874,842 filed on Apr. 27, 1992.

88-C0053 awarded by the Air Force Office of Scientific Research. Accordingly, the United States Government has certain rights in the present invention.

This invention was made with United States Government support under AFOSR Numbers F49620-85-C0013/F49620

FIELD OF THE INVENTION

The present invention is directed to a rapid and sensitive method for detecting Ureaplasma urealyticum using U. urealyticum-specific probes and oligonucleotides. In particular a target sequence can be amplified by in vitro nucleic acid amplification techniques or directly detected by nucleic acid hybridization using the subject probes and oligonucleotides. U. urealyticum-specific nucleic acids which do not recognize or hybridize to genomic nucleic acid of other Mycoplasma species are also provided.

BACKGROUND OF THE INVENTION

Ureaplasma urealyticum is a mycoplasma which has emerged as a suspected pathogen in fetuses and infants as well as in the adult genitourinary tract. U. urealyticum is often transmitted by sexual contact and can be transmitted to neonates born of infected mothers. This pathogen can also cause in utero infection of a fetus and has been isolated from amniotic fluid at stages of gestation as early as 16 weeks post-fertilization. In adults, U. urealyticum has been implicated as a cause of urethritis, urethroprostatitis, pelvic inflammatory disease, infertility and chorioamnionitis. In infants, U. urealyticum contributes to low birth weight and, more significantly, to infantile chronic lung disease. [See reviews by Cassell et al. (1991) Clin. Perinatol. 18:241–262; Cassell et al. (1984) Adv. Exp. Med. Biol. 224:93–115; and Cassell et al. (1983) Sex. Transm. Dis. 10:294–302.]

Ureaplasma range in size from 0.2 to 0.8 μm in diameter and are among the smallest of all free living organisms. Ureaplasma are difficult to culture because of their fastidious nutritional requirements and slow growth rates. Such properties render the current cultural diagnostic procedures for Ureaplasma difficult and time consuming, requiring up to 2 to 6 days for positive identification depending on the amount of the initial inoculum. Since diagnosis of Ureaplasma infection by such methods is time consuming, expensive and requires a high degree of bacteriological expertise, few clinical laboratories include U. urealyticum in the list of organisms for which they provide detection services. These disadvantages often discourage physicians from requesting diagnostic tests for U. urealyticum and result in a considerable loss of time in treatment of patients. Consequently, the etiologic role of U. urealyticum in various diseases and the complete range of tissue tropism for this pathogen has not been elucidated.

U. urealyticum-specific nucleic acid probes offer an approach to surmount the difficulties inherent in identification and detection of U. urealyticum by traditional bacteriological culture technology. Specific nucleic acid probes for U. urealyticum are thus useful in conventional hybridization detection procedures, as well as in other procedures, such as in situ hybridization, solution hybridization and in combination with in vitro nucleic acid amplification and subsequent detection. The latter method for U. urealyticum detection provides a practical means to enhance detection sensitivity relative to conventional hybridization technology.

Whereas the sequences of the U. urealyticum 5S and 16S RNA sequences are known [Rogers et al. (1985) Proc. Natl. Acad. Sci. USA 82:1160–1164; Weisberg et al. (1989) J. Bacteriol. 171:6455–6467], there has been no publication of a nucleotide sequence which is specific for U. urealyticum and has demonstrated utility to detect U. urealyticum in animals and patients.

SUMMARY OF THE INVENTION

The present invention provides a rapid and sensitive method for detection of U. urealyticum in animals, especially in human and veterinary clinical samples. In particular, the present invention provides nucleic acid probes and oligonucleotides with demonstrated specificity for U. urealyticum over other Mycoplasma species. These subject probes and oligonucleotides are then used in a detection assay to establish whether U. urealyticum microorganisms are present in a sample.

In one embodiment, the method of detecting U. urealyticum uses in vitro nucleic acid amplification to increase the assay sensitivity by amplifying a U. urealyticum target nucleic acid by contacting a sample with at least one U. urealyticum-specific oligonucleotide for a time and under conditions sufficient for the oligonucleotide(s) to hybridize to the target nucleic acid to permit amplification and thereby to produce RNA or DNA copies of the target nucleic acid, and detecting such RNA or DNA coipes. Preferred means of in vitro nucleic acid amplification include the polymerase chain reaction (PCR), the transcription-based amplification system (TAS), the self-sustained sequence replication (3SR) system, the ligase-based amplification system (LAS), the QB replicase RNA replication system and transcription.

In another embodiment, the method of detecting U. urealyticum is by nucleic acid hybridization by contacting a U. urealyticum target nucleic acid with a U. urealyticum-specific nucleic acid probe for a time and under conditions sufficient for the probe to hybridize to the target nucleic acid and detecting or measuring such hybridization. Preferred forms of nucleic acid hybridization include solid-phase-based hybridization, i.e. hybridization on filters or beads, solution phase hybridization, and in situ hybridization.

A further aspect of this invention provides kits for practicing the methods described herein.

DETAILED DESCRIPTION OF THE INVENTION

The present invention relates to detection of a small microorganism, *U. urealyticum*, which has been associated with a variety of human disease conditions including urethritis, urethroprostatitis, pelvic inflammatory disease, infertility and chorioamnionitis, as well as low birth weight and chronic lung disease in infants.

In particular, the present invention provides isolated nucleic acid which is specific for detection of *U. urealyticum*. Such nucleic acid can be selected from a genomic library of *U. urealyticum* DNA by its capability of hybridizing with *U. urealyticum* nucleic acid but not with nucleic acid from such Mycoplasma species as *Mycoplasma genitalium, Mycoplasma hominis, Mycoplasma hyorhinis, Mycoplasma orale, Mycoplasma pneumoniae* and *Mycoplasma salivarium*. For example, a genomic library of *U. urealyticum* DNA can be screened by using a labeled probe made from *U. urealyticum* genomic DNA and then screening the library again with a labeled probe made from genomic DNA obtained from the above-recited Mycoplasma. In this manner, *U. urealyticum*-specific nucleic acid can be identified. Construction of genomic libraries, screening procedures and general recombinant DNA techniques for the present invention can be found in any of many texts or manuals available for such procedures. One such manual is provided by Sambrook, et al. (1989) *Molecular Cloning: A Laboratory Manual*, Vols. 1–3, Cold Spring Harbor Press, Cold Spring Harbor, N.Y.

Accordingly, preferred nucleic acids of the present invention include the *U. urealyticum* DNA inserts in plasmids pUP18, pCU3900, pCU2800 and pCU700. pUP18 is pBR322 containing three *U. urealyticum* PstI restriction fragments of 700, 2800 and 3900 base pairs (bp). Each of these three fragments have been subcloned into the PstI site of pUC119 to produce pCU700, pCU2800 and pCU3900, respectively. The 3900 bp insert in pCU3900 (and pUP18) has been partially sequenced and this partial sequence is identified herein as SEQ ID NO:1. SEQ ID NO:1 does not encode an open reading frame. Plasmid pCU3900 was deposited with the American Type Culture Collection, 12301 Parklawn Drive, Rockville, Md. on Jan. 18, 1996 and was assigned accession number 97424.

The isolated nucleic acids of the present invention also include regions or segments of the *U. urealyticum* genome which do not encode an open reading frame, or a polypeptide, since such non-coding regions may be more highly diverged from corresponding regions in closely related species than are coding regions.

The present invention includes nucleic acid probes and oligonucleotides derived from the subject *U. urealyticum*-specific nucleic acids. Any of these nucleic acids, probes or oligonucleotides can have a nucleotide sequence which is sufficiently complementary to hybridize to a nucleotide sequence derived from genomic *U. urealyticum* DNA but not to genomic DNA from *M. genitalium, M. hominis, M. hyorhinis, M. orale, M. pneumoniae* and *M. salivarium*.

Accordingly, preferred nucleic acid probes and oligonucleotides also include the *U. urealyticum* DNA in pUP18, pCU3900, pCU2800, pCU700 and the rDNA-specific sequences provided by SEQ ID NOS:4–9

Complementarity between nucleic acids is the degree to which the bases in one nucleic acid strand can hydrogen bond, or base pair, with the bases in a second nucleic acid strand. Hence, complementarity can sometimes be conveniently described by the percentage, i.e. proportion, of nucleotides which can form base pairs between two nucleic acid strands or within a specific region or domain of the two strands.

As used herein, sufficiently complementary means that the subject *U. urealyticum* nucleic acid has a sufficient number of the nucleotides, but not necessarily all, to form base pairs with nucleotides in an *U. urealyticum* nucleic acid. The number of base pairs necessary is that number of base pairs which provide detectable hybridization to the *U. urealyticum* nucleic acid with little or no detectable hybridization to the related Mycoplasma species listed herein. Therefore, the degree of complementarity that the present oligonucleotides and isolated nucleic acids have with the *U. urealyticum* genome need not be 100% so long as selective hybridization to *U. urealyticum* can be achieved and detected.

When expressed or measured by percentage of base pairs formed, the degree of complementarity can range from as little as about 70% complementarity to full, i.e. 100% complementarity. In general, the overall degree of complementarity between a U. urealyticum RNA or DNA and the synthesized DNA fragments, oligonucleotides and nucleic acids of the present invention is at least about 80%, and preferably about 90% or higher.

Nucleic acids, probes and oligonucleotides can be prepared by conventional methods, for example, by recombinant techniques or by synthetic techniques. Recombinant techniques include isolation of restriction fragments, nick translation and other known techniques, for example, as provided by Sambrook et al. Oligonucleotides can be made by any of a myriad of procedures known for making DNA or RNA oligonucleotides. For example, such procedures include enzymatic synthesis and chemical synthesis.

Enzymatic methods of DNA oligonucleotide synthesis frequently employ Klenow, T7, T4, Taq or *E. coli* DNA polymerases as described in Sambrook et al. Enzymatic methods of RNA oligonucleotide synthesis frequently employ SP6, T3 or T7 RNA polymerase as described in Sambrook et al. Reverse transcriptase can also be used to synthesize DNA from RNA (Sambrook et al.). To prepare an oligonucleotide enzymatically requires a template nucleic acid which can either be synthesized chemically, or be obtained as mRNA, genomic DNA, cloned genomic DNA, cloned cDNA or recombinant DNA. Some enzymatic methods of DNA oligonucleotide synthesis can require an additional primer oligonucleotide which can be synthesized chemically.

Chemical synthesis of oligonucleotides is well known in the art and can be achieved by solution or solid phase techniques. Moreover, oligonucleotides of defined sequence can be purchased commercially or can be made by any of several different synthetic procedures including the phosphoramidite, phosphite triester, H-phosphonate and phosphotriester methods, typically by automated synthesis methods. Modified bases can also be incorporated into the oligonucleotide, and particularly if modified phosphodiester linkages are used, then the synthetic procedures are altered as needed according to known procedures. In this regard, Uhlmann et al. [(1990) Chemical Reviews 90:543–584] provide references and outline procedures for making oligonucleotides with modified bases and modified phosphodiester linkages.

After enzymatic or chemical synthesis, oligonucleotides may be purified by polyacrylamide gel electrophoresis, or by any of a number of chromatographic methods, including gel chromatography and high pressure liquid chromatography. To confirm a nucleotide sequence, oligonucleotides may be subjected to DNA sequencing by any of the known procedures, including Maxam and Gilbert sequencing, Sanger sequencing, capillary electrophoreses sequencing the wandering spot sequencing procedure or by using selective chemical degradation of oligonucleotides bound to Hybond paper. Sequences of short oligonucleotides can also be analyzed by plasma desorption mass spectroscopy or by fast atom bombardment [McNeal et al. (1982) *J. Am. Chem. Soc.* 104:976; Viari et al. (1987) *Biomed. Environ. Mass Spectrom.* 14:83; Grotjahn et al. (1982) *Nucleic. Acid Res.* 10:4671). Sequencing methods are also available for RNA oligonucleotides.

Another aspect of this invention provides a method of detecting *Ureaplasma urealyticum* involving in vitro nucleic acid amplification which comprises:

(a) amplifying a *U. urealyticum* target nucleic acid by contacting a sample to be tested for the presence of *U. urealyticum* with at least one oligonucleotide for a time and under conditions sufficient to produce RNA or DNA copies of the target nucleic acid; wherein the oligonucleotide comprises a nucleotide sequence selected from genomic *U. urealyticum* DNA such that the oligonucleotide is sufficiently complementary to hybridize to the target nucleic acid to permit amplification thereof; and wherein the oligonucleotide does not hybridize to genomic DNA of *M. genitalium, M. hominis, M. hyorhinis, M. orale, M. pneumoniae* or *M. salivarium*; with the proviso that said *U. urealyticum* DNA does not encode ribosomal RNA; and (b) detecting said copies.

Additionally, the present invention provides a method of detecting *U. urealyticum* as above wherein the oligonucleotide comprises a nucleotide sequence selected from genomic *U. urealyticum* DNA such that the oligonucleotide is sufficiently complementary to hybridize to the target nucleic acid to permit amplification thereof; and wherein the oligonucleotide does not hybridize to genomic DNA of *M. genitalium, M. hominis, M. hyorhinis, M. orale, M. pneumoniae* and *M. salivarium*.

As used herein, the method of amplifying *U. urealyticum* target sequences are methods of in vitro nucleic acid amplification which include any procedure using an oligonucleotide to direct synthesis of a DNA or RNA copy of the target sequence. In vitro nucleic acid amplification thus allows selective synthesis of a specific DNA or RNA target relative to the complex bulk of nucleic acid present in a sample. The specificity of the process is determined by the oligonucleotides, e.g. oligonucleotide primers, capable of hybridizing with the *U. urealyticum* nucleic acid to the exclusion of nucleic acids from Mycoplasma species.

In vitro nucleic acid amplification techniques are known in the art. A review of such techniques is found in Kwoh et al. (1990) *Am. Biotechnol. Lab.* 8:14. In vitro nucleic acid amplification techniques include PCR, TAS, 3SR, LAS, Qβ RNA replication system and run-off transcription.

PCR is a method for primer-directed enzymatic amplification of target nucleic acids. PCR synthesis occurs by repeated cycles of heat denaturation of the target, primer annealing and primer extension. These cycles can be performed manually or, preferably, automatically. Thermal cyclers such as the Perkin-Elmer Cetus cycler are specifically designed for automating the PCR process, and are preferred. The number of cycles per round of synthesis can be varied from 2 to more than 50, and is readily determined by considering the source and amount of the nucleic acid template, the desired yield and the procedure for detection of the synthesized DNA fragment. PCR techniques and many variations of PCR are known. Basic PCR techniques are described by Saiki et al. (1988 *Science* 239:487–491 and by U.S. Pat. Nos. 4,683,195; 4,683,202 and 4,800,159 (which are incorporated herein by reference).

The transcription-based amplification system (TAS) utilizes a sample (sense) RNA template from which a double stranded complementary DNA (i.e. cDNA) is made. One or more of the oligonucleotides used for synthesis of the cDNA contains an RNA polymerase recognition site. An RNA polymerase capable of recognizing and synthesizing RNA starting at that recognition site is then added to produce many RNA copies of the cDNA. To achieve even greater amounts of an RNA synthetic product, additional rounds of cDNA synthesis can be performed using the synthesized RNA as template and this additional cDNA can be used to make even more RNA product. RNA polymerases which can be used for TAS include, for example, SP6, T3, T7 and other RNA polymerases. TAS techniques are described by Kwoh et al.

In this regard, the subject oligonucleotides can contain an additional sequence which encodes an RNA polymerase recognition (binding) site. Such sites are well known in the art and readily determined by one of ordinary skill in the art.

The self-sustained sequence replication (3SR) procedure involves continuous cycling of reverse transcriptase and RNA polymerase synthesis. 3SR utilizes RNase H enzymatic degradation of the RNA in an RNA:cDNA duplex, an innovation which eliminates thermal denaturation and repetitive addition of reagents. The 3SR procedure involves synthesis of a double stranded cDNA wherein the oligonucleotide used for synthesis of either the first or second cDNA strand, has an RNA polymerase recognition site. The double-stranded cDNA then acts as target for synthesis of either an antisense or sense RNA, depending on whether the first or second cDNA strand, respectively, has the RNA polymerase recognition site. Since there is no thermal denaturation step, the enzymes used for cDNA synthesis remain active and can produce more cDNA from the sense or antisense RNA product which can itself serve as a target for more RNA product. 3SR techniques are described by Kwoh et al.

The 3SR procedure has some advantages over PCR or TAS in that all reagents are placed in a single tube and incubation is at a single temperature. Accordingly, no thermal cycling or repeated addition of reagents is required. 3SR is also more rapid than many other in vitro nucleic acid amplification procedures since an approximate $10^6$-fold amplification of a desired DNA or RNA can be achieved in about an hour.

DNA ligase can be used to synthesize DNA by repeatedly joining oligonucleotides hybridized to a template nucleic acid. Such procedures have been termed ligation amplification (LAR) and ligase-based amplification systems (LAS). LAR or LAS utilizes four oligonucleotides wherein two oligonucleotides hybridize to one strand of the target DNA and the other two hybridize to the complementary sequences. The adjacently hybridizing oligonucleotides are then joined by DNA ligase. After thermal denaturation, an additional cycle of hybridization and ligation can be performed. Each round of denaturation, hybridization and ligation increases the ligated product by about two-fold. Blunt end ligation of oligonucleotides hybridizing to complementary oligonucleotides can be controlled by adjusting the temperature of the ligation step. The LAS technique is described by Kwoh et al.

An RNA can be synthesized from a target by employing a Qβ replicase RNA replication system in which a first strand of a cDNA is made having a Qβ replicase 5'-recognition site lying on the 3'-side of an RNA polymerase recognition site. This is done with an oligonucleotide capable of hybridizing to an RNA target which also encodes the 5'-Qβ and RNA polymerase recognition sites in the correct positions. A second cDNA strand is then synthesized using an oligonucleotide encoding a Qβ 3'-recognition site. An RNA polymerase can then use the double-stranded cDNA as a template for synthesis of antisense RNA having, as 5' and 3' ends, the respective 5'- and 3'-Qβ replicase recognition sites. This antisense RNA can then serve as a template for Qβ replicase synthesis of both sense and antisense RNA. This Qβ replicase technique is described by Kwoh et al.

In this regard, the subject oligonucleotides can contain additional nucleotide sequences which encode an RNA polymerase recognition site, the 5' Qβ replicase recognition site and the 3' Qβ replicase recognition site as necessary to conduct Qβ replicase RNA replication system. Such sites are well known in the art and can readily be incorporated in the oligonucleotides of the present invention.

Preferably, the oligonucleotides for use in detecting *U. urealyticum* are oligodeoxynucleotides whose length depends on many factors including the nucleotide sequence and the temperature at which these oligonucleotides are hybridized and used for DNA or RNA synthesis. The considerations necessary to determine the length of the oligonucleotides are well known to the skilled artisan. Oligonucleotides of the present invention typically contain about 15–150 or more nucleotides.

A suitable amount of each oligonucleotide for in vitro nucleic acid amplification to enable detection of *U. urealyticum* is about 1 pmole to 100 pmole and preferably about 10 pmole to 50 pmole. An especially preferred amount of each oligonucleotide is about 20–30 pmole. Other reagents as needed are added to the amplification reaction mixtures. Such reagents include nucleotides, additional enzymes, a source of a high-energy phosphate (e.g. ATP), and the like. Moreover the target nucleic acid can be either DNA, RNA or both and depends on the in vitro nucleic acid amplification system selected. In many of these procedures DNA is the preferred template.

Enzymes which used for in vitro nucleic acid amplification include *Escherichia coli* DNA polymerase I, Klenow fragment of *E. coli* DNA polymerase I, T4 DNA polymerase, T7 DNA polymerase, *Thermus aquaticus* DNA polymerase, *Thermococcus litoralis* DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *E. coli* DNA ligase or Qβ replicase.

The preferred oligonucleotides for the present method include oligonucleotides having a sufficiently complementary nucleotide sequence derived from the *U. urealyticum* DNA inserts of pUP18, pCU3900, pCU2800 or pCU700. More particularly, the preferred oligonucleotides have a sequence from SEQ ID NO:1. In one preferred embodiment, oligonucleotides having SEQ ID NO:2 and SEQ ID NO:3 are used in PCR to amplify a 186 bp DNA fragment (portion) from SEQ ID NO:1. This portion of SEQ ID NO:1 is nucleotides 11 to 197, inclusive. Any of these nucleotide can have additional sequences which encode an RNA polymerase recognition site or the Qβ replicase recognition sites in the configuration necessary to practice in vitro nucleic acid amplification.

As used herein a sample can be an animal body fluid, animal secretions, an animal tissue, a culture medium or a transport medium. Animals include humans, domestic animals, farm animals and pets. As used herein animals also include adult, neonate and infant patients.

According to the present invention, animal body fluids include blood, urine, semen, vaginal secretions, amniotic fluid, saliva, mucus, pulmonary fluids and the like. Especially preferred body fluids include urine, semen, vaginal secretions, amniotic fluid, saliva and pulmonary fluids. Animal secretions include fecal matter.

As used herein animal tissues include tissues such as lung, bronchial and urogenital tissues. Urogenital tissues include tissues obtained during medical procedures, especially urethral, bladder, kidney, prostatic, vaginal, cervical, uterine and similar tissues.

As used herein, culture medium includes any solution for growth of a prokaryotic or eukaryotic cell. For example, the present oligonucleotides, nucleic acids and methods can be used to detect *U. urealyticum* contamination in cultured eukaryotic cells separately or in conjunction with known tests for detection of Mycoplasma contamination.

Similarly, transport medium samples include solutions for transport of a prokaryotic or eukaryotic cell, but can also include solutions used during transport of an animal body fluid, secretion, or tissue.

Detection of the amplified *U. Urealyticum* target nucleic acid (i.e. the RNA or DNA copies of the target) can be accomplished by conventional nucleic acid hybridization techniques. Such techniques include solid-phase-based hybridization and solution hybridization using a variety of reporter molecules. The detailed methodology for some of these techniques can be found in Sambrook et al., Diamandis et al., Landegren et al., and Wolcott et al. [Diamandis et al. (1990) *Clin. Chim. Acta.* 194:19–50; Landegren et al. (1988) *Science* 242:229–237; Wolcott et al. (1991) *J. Food Protect.* 54:387–401] and is further described hereinbelow.

Another aspect of this invention provides a method of detecting *Ureaplasma urealyticum* by nucleic acid hybridization which comprises:

(a) contacting a *U. urealyticum* target nucleic acid from a sample to be tested for the presence of *U. urealyticum* with a nucleic acid probe for a time and under conditions sufficient to permit hybridization between the probe and the target nucleic acid; wherein the probe comprises a nucleotide sequence selected from genomic *U. urealyticum* DNA such that the probe is sufficiently complementary to hybridize to the target nucleic acid; and wherein the probe does not hybridize to genomic DNA of *M. genitalium, M. hominis, M. hyorhinis, M. orale, M. pneumoniae* or *M. salivarium*; with the proviso that the *U. urealyticum* DNA does not encode ribosomal RNA; and (b) detecting or measuring the hybridization.

Additionally, the present invention provides a method of detecting *U. urealyticum* as above wherein the probe comprises a nucleotide sequence selected from genomic *U. urealyticum* DNA such that the probe is sufficiently complementary to hybridize to the target nucleic acid and wherein the probe does not hybridize to genomic DNA of *M. genitalium, M. hominis, M. hyorhinis, M. orale, M. pneumoniae* and *M. salivarium.*

Preferred nucleic acid probes of the present invention are the *U. urealyticum* DNA inserts in pUP18, pCU3900, pCU2800 and pCU700 and nucleic acids probes which are sufficiently complementary to hybridize to target nucleic acids containing these sequences. More particularly, preferred nucleic acid probes have SEQ ID No:1, SEQ ID NO:2 or SEQ ID NO:3 or variations of these sequences which are sufficiently complementary to detect a target nucleic acid containing such sequences.

Another set of preferred nucleic acid probes include probes having SEQ ID NO:4, SEQ ID NO:5, SEQ ID NO:6, SEQ ID NO:7, SEQ ID NO:8 or SEQ ID NO:9. Probes having sufficient complementarity to hybridize to these sequences are also included as preferred embodiments. The probes of SEQ ID NOS:4–7 are derived from 16S rRNA sequences and probes of SEQ ID NOS: 8 and 9 are derived from 5S rRNA sequences of *U. urealyticum* DNA.

Nucleic acid hybridization as used herein includes solid phase-based hybridization (heterogeneous methods), solution phase hybridization (homogeneous methods) and in situ hybridization. All these methods are known to the skilled artisan and readily modified for use with the subject *U. urealyticum*-specific probes. There are many variations on these techniques which are possible and included herein; many of these techniques are described by Sambrook et al., Diamandis et al., Landegren et al. and Wolcott et al.

The samples for use in the present method of nucleic acid hybridization to detect *U. urealyticum* are the same as those desribed to detect *U. urealyticum* after in vitro nucleic acid amplification.

Detection of *U. urealyticum*, whether or not amplification of the target has been done, using the probes of the present invention can be by a variety of hybridization techniques which are well known in the art, including Southern and Northern hybridization to RNA or DNA obtained from clinical samples, and in situ hybridization to tissues or cells which may be infected by *U. urealyticum*. Methods for performing such techniques are available, for example, in Sambrook et al.

*U. urealyticum* can be detected in sample nucleic acids which have or have not undergone purification. For example, RNA or DNA can be extracted from samples using techniques available in the art, then immobilized onto nitrocellulose or nylon filters, and well-known filter hybridization techniques may be employed for detection of *U. urealyticum* nucleic acids. However, sample nucleic acids need not be purified. For example, sample cells can simply be lysed and cellular RNA or DNA fixed unto a filter. Sample RNA and DNA can also be size fractionated through a gel before fixation onto a filter, or simply dot blotted unto a filter.

In situ hybridization can be performed by procedures known in the art, for example as disclosed in Gall et al. (1969) *Proc. Natl. Acad. Sci. USA* 63:378–83; Giovannoni et al. 1988 *J. Bacteriol.* 170:720–726; or DeLong et al. (1990) *Diag. Clin. Test.* 28:41–44.

According to the present invention, a probe of the subject isolated nucleic acids, nucleic acid probes or oligonucleotides of the present invention, can be labelled by any procedure known in the art, for example by incorporation of nucleotides linked to a "reporter molecule". A "reporter molecule", as used herein, is a molecule which provides an analytically identifiable signal allowing detection of the hybridized probe. Detection may be either qualitative or quantitative. Commonly used reporter molecules include fluorophores, enzymes, biotin, chemiluminescent molecules, bioluminescent molecules, avidin, streptavidin or radioisotopes. Fluorophores that are readily available and suitable for the methods of the present invention include fluorescein isothiocyanate (FITC), rhodamine red and the like. Commonly used enzymes include horseradish peroxidase, alkaline phosphatase, glucose oxidase and β-galactosidase, among others. Enzymes can be conjugated to avidin or streptavidin for use with a biotinylated probe. Similarly, nucleic acids can be conjugated to avidin or streptavidin for use with a biotinylated enzyme. The substrates to be used with these enzymes are generally chosen for the production, upon hydrolysis by the corresponding enzyme, of a detectable color change. For example, p-nitrophenyl phosphate is suitable for use with alkaline phosphatase reporter molecules; for horseradish peroxidase, 1,2-phenylenediamine, 5-aminosalicyclic acid or tolidine are commonly used.

Incorporation of a reporter molecule into DNA can be by any method known to the skilled artisan, for example by nick translation, primer extension, random oligo priming, by 3' or 5' end labeling or by other means (see, for example, Sambrook et al.).

Incorporation of a reporter molecule into RNA can be by synthesis of *U. urealyticum*-specific RNA using T3, T7, Sp6 or other RNA polymerases (Sambrook et al.). Such enzymes require a *U. urealyticum*-specific DNA template having the appropriate RNA polymerase start signals at sites flanking the template. These start signals can be juxtaposed to the DNA template by insertion of the DNA template into a vector having start signals flanking the insertion site. Suitable vectors having such start signals include pGEM (Promega Biotec), pBluescript (Vector Cloning Systems), pSP6 (Bethesda Life Technologies), Gene Scribe® (U.S. Biochem. Corp.) and related vectors.

A preferred in situ hybridization-labeled probe is prepared by covalent linkage of a fluorescent reporter molecule to the subject nucleic acid probe or the oligonucleotide. Moreover, preferred labeled probes are prepared from the oligonucleotides of the present invention.

In a preferred embodiment, in situ hybridization is performed on sample body fluids such as blood, urine, amniotic fluid, semen, vaginal secretions and pulmonary fluid. Clinical specimens of these fluids are obtained and cellular and microbial material is sedimented. Cell smears can be prepared on a standard microscope slide, then fixed with an appropriate fixative. The labeled probe then is applied to the slide and slides are incubated at a suitable hybridization temperature (generally 15° to 55° C.) for 1–20 hours. Non-hybridized probe is then removed by extensive, gentle washing at an appropriate stringency.

When a fluorescent reporter molecule is used, the slide is mounted in an appropriate medium, such as SAVA mounting fluid, and the fluorescence is observed under a fluorescent microscope. If an enzyme is used as a reporter molecule, a suitable substrate or substrates are applied. The slide can then be incubated at an appropriate temperature for a time appropriate to allow a detectable color signal to appear when the slide is examined by light microscopy. Alternatively, if the probe is radioactively labeled, hybridized slides can be dipped in photoemulsion, and the signal detected as visible silver-grains under the light microscope.

In yet a further aspect the present invention provides a compartmentalized kit for detection of *U. urealyticum*. This kit can be adapted to facilitate detection by a method involving a first step of in vitro nucleic acid amplification followed by detecton of the amplified fragment or by a method of nucleic acid hybridization in accordance with the invention. The kit has a first container adapted to contain at least one of the subject oligonucleotides for in vitro nucleic acid amplification. Alternatively, the first container is adapted to contain at least one of the subject nucleic acid probes for nucleic acid hybridization.

In this regard the first container of the kit can contain an isolated nucleic acid specific for *U. urealyticum* including pUP18, pCU3900, pCU2800, pCU700 or fragments thereof. Likewise the first container can contain an isolated nucleic acid comprising a nucleotide sequence of SEQ ID NO:1 or a fragment thereof, or SEQ ID NOS:2–9. When the kit is used for PCR, the preferred nucleic acids are two oligonucleotides, one having the sequence of SEQ ID NO:2 and the other of SEQ ID NO:3. When the kit is used for nucleic acid detection, it contains a probe having the sequence of SEQ ID NOS:5–7 or 9.

The kit can also be adapted to contain another container having an *U. urealyticum* nucleic acid at a known concentration to act as a standard or positive control. Suitable *U. urealyticum* nucleic acid for use as standards or positive controls include any of the present oligonucleotides or isolated nucleic acids, *U. urealyticum* genomic DNA, mRNA, rRNA, tRNA or the like. A preferred standard or positive control is *U. urealyticum* rRNA, *U. urealyticum* genomic DNA or an isolated DNA having SEQ ID NO:1.

The compartmentalized kit can also have another container adapted to contain a reagent for synthesis of the DNA or RNA by in vitro nucleic acid amplification. For example, such a reagent can be an enzyme or a mixture of nucleotides and can include any salts and cofactors required by the enzyme for synthesis of the DNA or RNA segment. Some of the enzymes contemplated by the present invention for synthesis of DNA or RNA include *E. coli* DNA polymerase I, Klenow fragment of *E. coli* DNA polymerase I, T4 DNA polymerase, T7 DNA polymerase, *T. aquaticus* DNA polymerase, *T. litoralis* DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *E. coli* DNA ligase or Qβ replicase.

The examples further illustrate the invention.

EXAMPLE 1

MATERIALS AND METHODS

Bacterial strains

The following species of Mycoplasma were obtained from the American Type Culture Collection (Rockville, Md.): *U. urealyticum* ATCC 27618, *M. hominis* ATCC 23114, *M. orale* ATCC 23714, *M. genitalium* ATCC 33530, *M. pneumoniae* ATCC 15531, *M. salivarium* ATCC 33130, and *M. hyorhinis* ATCC 23839. Growth media and culture conditions were as described by Velleca et al. (1980) *Laboratory Diagnosis of Mycoplasma Infections*, Center for Disease Control, Atlanta, pp. 111–122.

Clinical Samples

Clinical isolates were obtained by standard methods [Walsh et al. (1991) *Pediatr. Infect. Dis. J.* 10:823–827]. The isolates were from fluid biopsy specimens of neonates and patients admitted to Wilford Hall USAF Medical Center, San Antonio, Tex., and David Grant Medical Center, Travis Air Force Base, Fairfield, Calif. Specimens were shipped in Mycotrans (Irvine Scientific, Santa Ana, Calif.) and then grown in Mycotrim GU media (Irvine Scientific), Remel 10B medium, or Remel Arginine broth to test for the presence of *U. urealyticum* and *M. hominis*, respectively. Species verification of *U. urealyticum* or *M. hominis* was accomplished on the basis of colony characteristics on Mycotrim GU medium, Dienes staining and biochemical reactions.

Library construction and screening of clones

A library was constructed using genomic DNA isolated from *U. urealyticum* ATCC 27618 by the method of Razin et al. (1983) *Int. J. Sys. Bacteriol.* 33:201–206. Digestion of this DNA with PstI was performed according to the manufacturer's instructions (GibcoBRL, Bethesda, Md.). Restriction fragments were ligated into PstI-hydrolyzed pBR322 using T4 DNA ligase as described by Sugino et al. (1977) *J. Biol. Chem.* 252:3987–3994. Competent *E. coli* DH5 cells were transformed using the procedure of Hanahan [(1983) *J. Mol. Biol.* 166:577–580] and then grown on Luria-Bertani (LB) agar containing 50 µg/ml tetracycline. The presence of *U. urealyticum* DNA caused insertional inactivation of the ampicillin resistance gene and such bacterial colonies appeared yellow when grown on Ampscreen® (GibcoBRL). Colonies harboring plasmids with an intact ampicillin resistance gene were blue in color. Recombinant plasmids were isolated by a miniprep boiling lysis method [Holmes et al. (1981) *Anal. Biochem.* 114:193–197]. Plasmid DNA was digested with restriction enzyme(s) and electrophoresed on standard 1% (w/v) agarose gels containing 1 µg/ml of ethidium bromide. DNA was visualized by UV fluorescence. The Ureaplasma insert DNA was sized by comparison with a standard 1 Kb ladder of DNA markers (GibcoBRL).

Selection of Ureaplasma-specific probe

DNA inserts liberated from recombinant plasmids were blotted onto Genescreen Plus® filters (NEN Research Products, Boston, Mass.) by Southern transfer [Southern (1975) *J. Mol. Biol.* 98:503–517). These immobilized inserts were tested for hybridization with *M. hominis* chromosomal DNA which had been labeled with biotin using the Oncor nonisotopic probe labeling kit (Oncor, Gaithersburg, Md.). Inserts which hybridized with *M. hominis* chromosomal DNA were visualized using a Sure Blot Nonisotopic Detection System (Oncor) and categorized as not being *U. urealyticum*-specific. Clones containing inserts which did not hybridize with *M. hominis* genomic DNA were initially presumed to contain *U. urealyticum*-specific DNA. *U. urealyticum* specificity was verified by using biotnylated Ureaplasm inserts as hybridization probes for PstI- or EcoRI-digested genomic DNA of various Mycoplasma species. Clones containing recombinant plasmids which only hybridized with restriction fragments from *U. urealyticum* genomic DNA were selected as *U. urealyticum*-specific probes.

DNA sequencing

The selected probes were isolated from pBR322 by excising the *U. urealyticum* insert with PstI followed by electrophoresis in a 1% agarose gel. DNA was extracted from the gel using GENECLEAN® (Bio 101, La Jolla, Calif.), ligated into pUC119, and the resulting ligation mix transformed into *E. coli* XL-1 Blues. Colonies containing recombinant plasmids were selected by growth on LB agar containing 60 µg/ml ampicillin in the presence of X-gal (5-bromo-4-chloro-3-indolyl-β-D-galactoside) and IPTG (isopropyl-β-D-thiogalactopyranoside). Plasmids were isolated from white colonies and a set of nested deletions was created using the Erase-a-Base System (Promega, Madison, Wis.) which is based upon the method of Henikoff (1984) *Gene* 28:351–359. These procedures permitted subcloning of smaller inserts having approximately 250 bp. Nucleotide sequences of the resulting smaller inserts were determined by the dideoxy chain termination method of Sanger using a Base Master Sequencing Kit (Pharmacia, Piscataway, N.J.).

EXAMPLE 2

UREAPLASMA UREALYTICUM-SPECIFIC PROBES

Figure 2A:
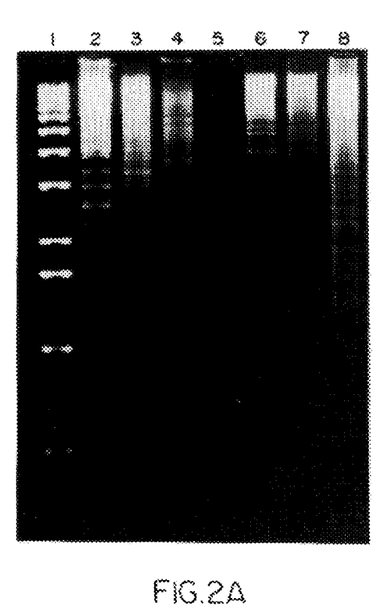
FIG. 2a shows EcoRI-digested genomic DNA from several Mycoplasma species and from U. urealyticum after separation in an 1% agarose gel.
Figure 2B:
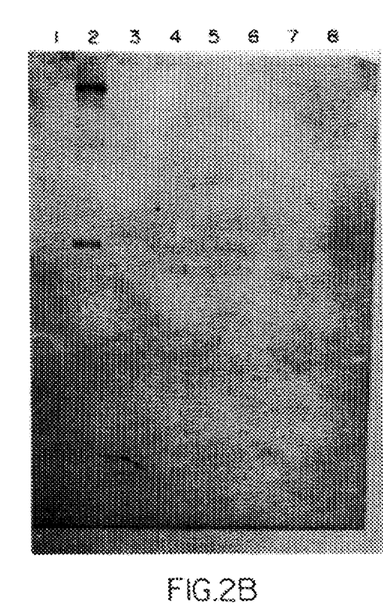
FIG. 2b shows an autoradiograph of a corresponding Southern blot probed with DNA from pCU3900. Lane 1 contains a 1 Kb ladder of DNA size markers. Lanes 2–8 contain genomic DNA from the following species: (2) U. urealyticum, (3) Mycoplasma genitalium, (4) *Mycoplasma hominis*, (5) *Mycoplasma hyorhinis*, (6) *Mycoplasma orale*, (7) *Mycoplasma pneumoniae*, and (8) *Mycoplasma salivarium*.

Several clones were obtained from a *U. urealyticum* genomic library which hybridized with total genomic DNA of *U. urealyticum* but not that of *M. hominis*. One clone in particular contained a plasmid designated pUP18 which hybridized with PstI-or EcoRI-hydrolyzed *U. urealyticum* DNA but not with similarly hydrolyzed DNA from other Mycoplasma species as described in Example 1. pUP18 contained three PstI inserts having sizes 700, 2800, and 3900 bp. Each of these PstI restriction fragment inserts was subcloned into pUC119 to produce pCU700, pCU2800 and pCU3900, respectively. The plasmid, pCU3900 was further analyzed since it provided the largest potential source for primer combinations. DNA in pCU3900 is highly specific for *U. urealyticum* genomic DNA. As depicted in FIG. 2, a probe made from the pCU3900 insert hybridized only with *U. urealyticum* genomic DNA and not with DNA from closely related Mycoplasma species *M. genitalium, M. hominis, M. hyorhinis, M. orale, M. pneumoniae*, or *M. salivarium*.

Figure 4:
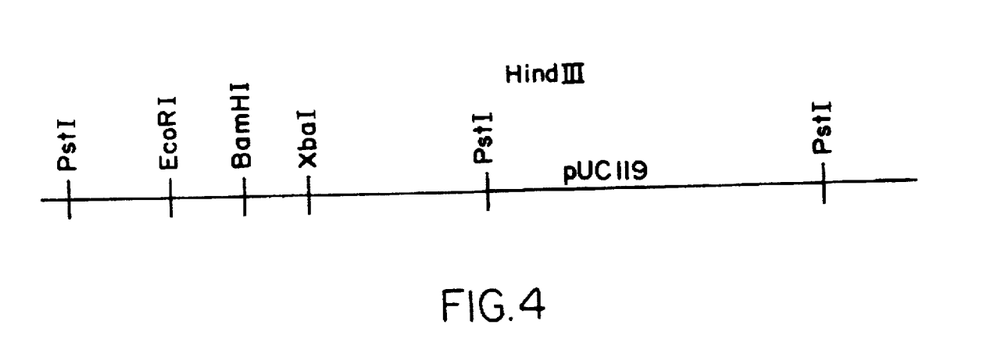
FIG. 4 shows a restriction map of pCU3900.

A restriction map of pCU3900 is shown in FIG. 4. The following restriction enzymes do not cut the PstI fragment of pCU3900: HindIII, KpnI, SalI, SstI and XhoI. The following restriction enzymes each cut the PstI fragment of pCU3900 one time: EcoRI, BamHI and XbaI. The EcoRI fragments of the PstI fragment of pCU3900 are about 0.9 and 2.92 kb; the BamHI fragments are about 1.65 and 2.30 kb; and the XbaI fragments are about 2.25 and 1.70 kb.

Sequencing and Analysis of the pCU3900

The Erase-a-Base system was used to generate a series of deletions in the pCU3900 *U. urealyticum* insert. Each of the deleted inserts was cloned into *E. coli* XL-1 Blues and used in determining the nucleotide sequence of the pCU3900 insert.

Partial sequencing of the 3900 bp insert was accomplished by the dideoxy chain termination method as described in Example 1. A 186 bp portion (positions 11–197) of SEQ ID NO:1 was selected as a possible target for PCR amplification. No significant homologies were found when this sequence or the oligonucleotide primers (SEQ ID NO: 2 or NO:3) were tested using the gene sequence analysis program of the Genetics Computer Group (GCG, University of Wisconsin, Madison Wis.).

EXAMPLE 3

PCR AMPLIFICATION OF U. UREALYTICUM-SPECIFIC DNA Selection of oligonucleotide primers The oligonucleotide primers which defined the target sequence consisted of 20 deoxyribonucleotides each. The sequence of these primers was 5'-ACTAAATTTATTGTTGTTAA-3' (SEQ ID NO:2) AND 5'-CAATGTAAATTCGTTTATCA-3' (SEQ ID NO:3). The suitability of these primers for specific PCR amplification of the target sequence and the determination of their individual properties were accomplished using the OLIGO software system (National Bioscience, Hamel, Minn.). Primers were synthesized by Midland Certified Reagent Company (Midland, Tex.).

PCR Amplification

The temperature and duration of each step in the PCR amplification cycle was determined from the melting temperatures of the primers.

DNA was extracted from mycoplasmacae contained in pure cultures or from clinical specimens of body fluids. Mycoplasma species tested include *U. urealyticum, M. hominis, M. orale, M. genitalium, M. pneumoniae , M. salivarium* and *M. hyorhinis*. A 1.5 ml culture or specimen sample was centrifuged in a microcentrifuge at 16,000×g for 10 min. The resulting pellet was air dried and then placed at −20° C. for future analysis. Prior to DNA synthesis by PCR, the frozen pellets were resuspended in 50 µl of sterile distilled water, boiled for 10 minutes, and then immediately placed on ice. DNA obtained from pure *U. urealyticum* cultures served as a positive control in all PCR analyses. Amplifications were performed using GeneAmp® PCR reagent kit with AmpliTaq® DNA polymerase (Perkin Elmer Cetus, Norwalk, Conn.). The PCR reactions contained 20 pmole of each primer (SEQ ID NOS: 2 and 3) and standard amounts of GeneAmp reagents. An overlay of mineral oil was added to each tube followed by 30 cycles of amplification on an Eppendorf Micro Cycler (Freemont, Calif.). Each cycle consisted of denaturation at 94° C. for 1 min, primer annealing at 50° C. for 2 min, and primer extension at 72° C. for 2 min and was conducted in sterile, disposable tubes to prevent cross contamination. The final cycle included a 10 min primer extension step to insure that all synthesized DNA fragments were completely extended. After amplification the mineral oil was removed from the aqueous PCR reagent mixture and 20 µl of the mixture was electrophoresed in a 4% (w/v) NuSieve GTG agarose gel (FMC, Rockland, Me.) containing 1 µg/ml of ethidium bromide. A 1 kb DNA Ladder and BioMarker Low Ladder (BioVentures, Murfreesboro, Tenn.) were used as size standards on gels. Linear regression analysis verified the size of the synthesized DNA fragment.

Figure 3:
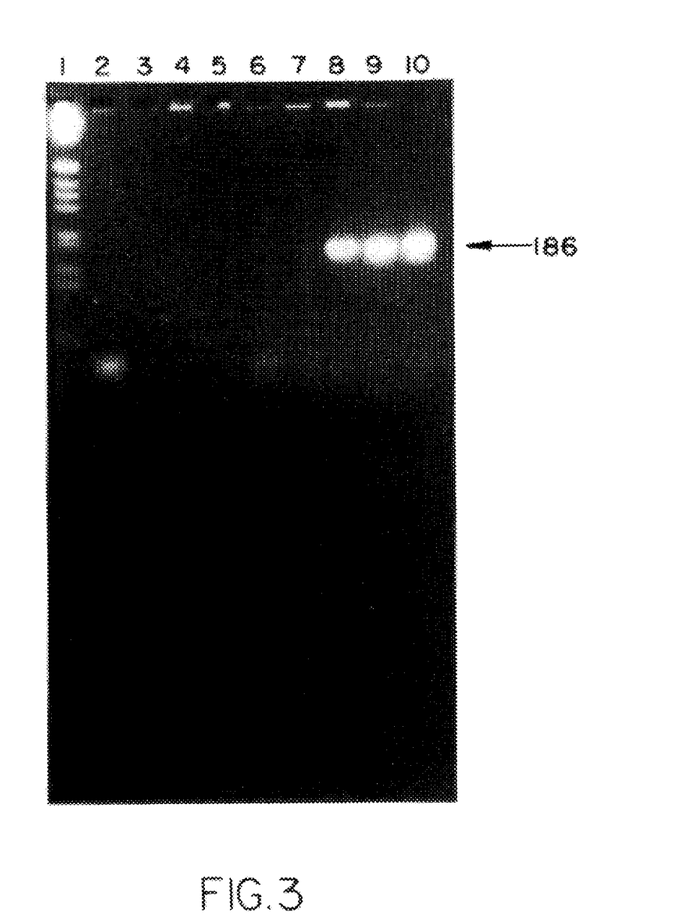
FIG. 3 shows the electrophoretic separation of the DNA fragments amplified by PCR using template genomic DNA obtained from (2) *M. genitalium*, (3) *M. salivarium*, (4) *M. hyorhinis*, (5) *M. hominis*, (6) *M. orale*, (7) *M. pneumoniae*, (8) *U. urealyticum*, and (9) and (10) clinical samples containing *U. urealyticum*. Lane (1) contains a 1 Kb ladder of DNA size markers.

As depicted in FIG. 3, the selected PCR conditions resulted in synthesis of a *U. urealyticum* DNA fragment from clinical samples derived from different sources, but did not result in synthesis of DNA from samples containing different Mycoplasma species.

EXAMPLE 4

IN SITU HYBRIDIZATION TO UREAPLASMA UREALYTICUM RNA

Preparation of Fluorescently Labeled Oligonucleotide Probes

Figure 1A:
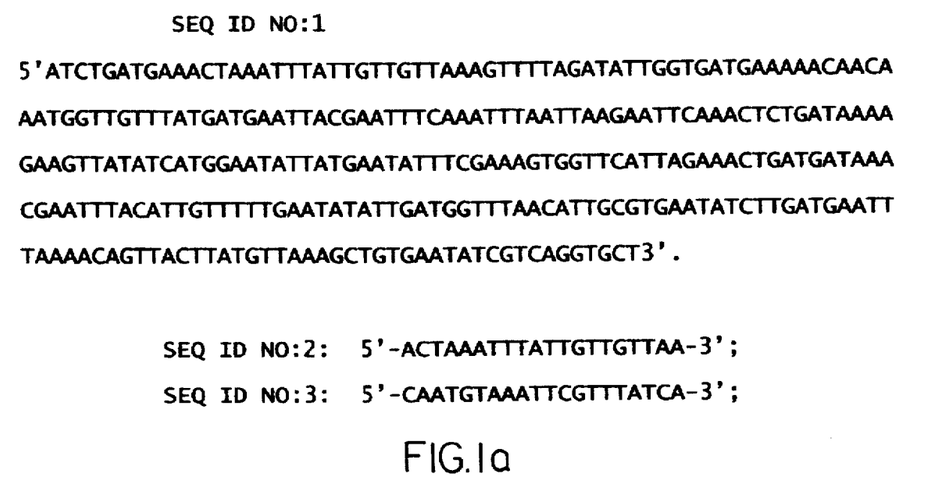
FIG. 1a depicts the sequence of an isolated U. urealyticum nucleic acid having SEQ ID NO:1 and of preferred oligonucleotides having sequences of SEQ ID NO:2 and SEQ ID NO:3.
Figure 1B:
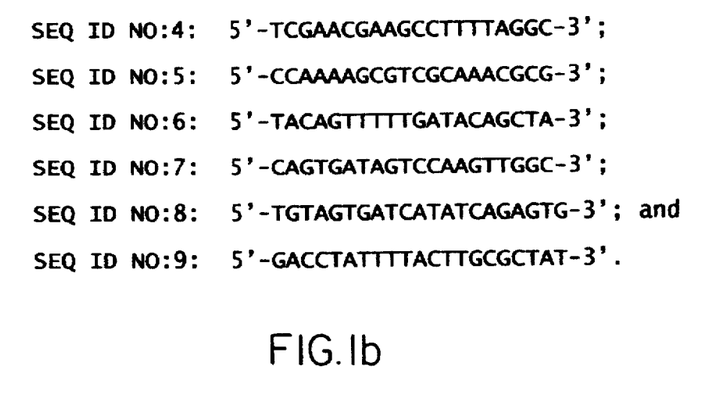
FIG. 1b depicts the sequences of oligonucleotides having SEQ ID NO:4, SEQ ID NO:5, SEQ ID NO:6, SEQ ID NO:7, capable of selective hybridization with U. urealyticum 16S rRNA, and the sequences of oligonucleotides having SEQ ID NO:8 and SEQ ID NO:9, capable of selective hybridization with U. urealyticum 5S rRNA.

Oligonucleotides having SEQ ID NOS: 5–7 and 9 (FIG. 1) were prepared for labeling with a fluorescent moiety by adding an amino group to the 5' end of the oligonucleotide. This was done during automated DNA synthesis by use of an Aminotink® reagent (Applied Biosystems, Foster City, Calif.) according to the following reaction:

Aminolink<sup>R</sup> Reagent

"Aminolinked"
Oligonucleotide

The aminolinked oligonucleotide was gel purified and then labeled with fluorescein isothiocyanate (FITC) under the manufacturer suggested conditions.

In Situ Hybridization of Oligonucleotide Probes

Cells in clinical samples were harvested at 14,000×g for 15 min to produce a visible cellular pellet. The pellet was resuspended in 50 µl of PBS (5.7M NaCl, 100 mM sodium phosphate, pH 7.5) and 5 µl of 37% formaldehyde was added. The cell suspension was spread on a poly-L-lysine coated slide and the cell smears were air dried at room temperature. The slides were either stored at −20° C. or processed immediately.

Slides were fixed in 3.7% formaldehyde and 90% methanol for 10 min at room temperature, washed briefly in distilled water, and placed in 100 mM Tris-HCl, pH 8.0, 50 mM Na borohydrate for 30 min in the dark with rapid stirring. The slides were then briefly rinsed with distilled water.

Slides were placed in hybridization solution (5× SET: 750 mM NaCl, 100 mM Tris-HCl, pH 7.8 and 5 mM EDTA; 0.1% SDS can be added to reduce background) for 1–20 hr. time. Hybridization was conducted with about 30 µl of 5×SET containing 50 ng of oligonucleotide probe (i.e., about 1.7 ng oligonucleotide/µl SET). After the hybridization solution was applied, a cover slip was placed on the slide and slides were incubated in a humid chamber at room temperature overnight.

Cover slips were removed by immersing the slide in 5× SET. The slides were washed 3 times for 10 min in 0.2× SET at 37° C. in the dark. Evans Blue (2% aqueous solution) was used as a counterstain to reduce background fluorescence. Slides were air dried before mounting with SAVA mounting fluid.

The presence of $U.$ $urealyticum$ infection was detected by observation of fluorescence within clinical sample cell smears using a fluorescent microscope.

What is claimed is:

1. A method of detecting *Ureaplasma urealyticum* involving in vitro nucleic acid amplification which comprises:

(a) amplifying a *U. urealyticum* target nucleic acid by contacting a sample to be tested for the presence of *U. urealyticum* with at least one oligonucleotide for a time and under conditions sufficient to produce RNA or DNA copies of said target nucleic acid, wherein said oligonucleotide is a fragment consisting of contiguous nucleotides of the *U. urealyticum* DNA inserted in pCU3900 having ATCC Accession Number 97424, or has a sequence having about 70% complementarity to and approximately the same length as said contiguous fragment, and wherein said oligonucleotide is sufficiently complementary to hybridize to said target nucleic acid to permit said amplification, and wherein said oligonucleotide does not hybridize to genomic DNA of *M. genitalium, M. hominis, M. hyorhinis, M. orale, M. pneumoniae* or *M. salivarium*; and (b) detecting said RNA or DNA copies, thereby detecting *Ureaplasma urealyticum*.

2. A method of detecting *Ureaplasma urealyticum* involving in vitro nucleic acid amplification which comprises:

(a) amplifying a *U. urealyticum* target nucleic acid by contacting a sample to be tested for the presence of *U. urealyticum* with at least one oligonucleotide for a time and under conditions sufficient to produce RNA or DNA copies of said target nucleic acid, wherein said oligonucleotide is selected from the group consisting of oligonucleotides having the sequence of SEQ ID NO:1, 2, 3, 6, 7, 8, 9 and fragments thereof consisting of contiguous nucleotides of said sequence wherein said oligonucleotide is sufficiently complementary to hybridize to said target nucleic acid to permit said amplification; and wherein said oligonucleotide does not hybridize to genomic DNA of *M. genitalium, M. hominis, M. hyorhinis, M. orale, M. pneumoniae* and *M. salivarium*; and (b) detecting said RNA or DNA copies, thereby detecting *Ureaplasma urealyticum*.

3. A method of detecting *Ureaplasma urealyticum* by nucleic acid hybridization which comprises:

(a) contacting a *U. urealyticum* target nucleic acid from a sample to be tested for the presence of *U. urealyticum* with a nucleic acid probe for a time and under conditions sufficient to permit hybridization between said nucleic acid probe and said target nucleic acid, wherein said nucleic acid probe consists of the *U. urealyticum* DNA inserted in pCU3900 having ATCC Accession Number 97424, a fragment consisting of contiguous nucleotides of said DNA inserted in said pCU3900, or a nucleic acid having 70% complementarity to and approximately the same length as said fragment, and wherein said probe is sufficiently complementary to hybridize to said target nucleic acid and wherein said probe does not hybridize to genomic DNA of *M. genitalium, M. hominis, M. hyorhinis, M. orale, M. pneumoniae* or *M. salivarium*; and (b) detecting or measuring said hybridization, thereby detecting *Ureaplasma urealyticum*.

4. A method of detecting *Ureaplasma urealyticum* by nucleic acid hybridization which comprises:

(a) contacting a *U. urealyticum* target nucleic acid from a sample to be tested for the presence of *U. urealyticum* with a nucleic acid probe for a time and under conditions sufficient to permit hybridization between said nucleic acid probe and said target nucleic acid, wherein said nucleic acid probe is selected from the group consisting of nucleic acids having the sequence of SEQ ID NO:1, 2, 3, 6, 7, 8, 9 and fragments thereof consisting of contiguous nucleotides of said sequence wherein said probe is sufficiently complementary to hybridize to said target nucleic acid and wherein said probe does not hybridize to genomic DNA of *M. genitalium, M. hominis, M. hyorhinis, M. orale, M. pneumoniae* and *M. salivarium*; and (b) detecting or measuring said hybridization, thereby detecting *Ureaplasma urealyticum*.

5. The method of claim 2 wherein two oligonucleotides are used and one oligonucleotide has the nucleotide sequence of SEQ ID NO:2 and the other oligonucleotide has the nucleotide sequence of SEQ ID NO:3.

6. The method of claim 3 or 4 wherein said hybridization is solid-phase-based hybridization, solution hybridization or in situ hybridization.

7. The method of claim 6 wherein said solid phase is a filter or bead.

8. The method of claim 6 wherein said hybridization is in situ hybridization.

9. The method of claim 1 or 2 wherein said oligonucleotide comprises an additional nucleotide sequence to facilitate said amplification.

10. The method of claim 9 wherein said sequence is an RNA polymerase binding site or a QB replicase binding site.

11. The method of claim 3 or 4 wherein a reporter molecule is attached to said nucleic acid probe.

12. The method of claim 11 wherein said reporter molecule is a fluorophore, a bioluminescent molecule, a chemiluminescent molecule, biotin, avidin, streptavidin, an enzyme or a radioisotope.

* * * * *